(12) United States Patent
Chen

(10) Patent No.: US 10,080,442 B2
(45) Date of Patent: Sep. 25, 2018

(54) SLEEP SUPPORT SYSTEM AND CONTROL METHOD THEREOF

(71) Applicant: Xilinmen Furniture Co., Ltd., Shaoxing (CN)

(72) Inventor: Ayu Chen, Shaoxing (CN)

(73) Assignee: XILINMEN FURNITURE CO., LTD., Industrial Park of Xilinmen, Yuecheng, Shaoxing (CN)

( * ) Notice: Subject to any disclaimer, the term of this patent is extended or adjusted under 35 U.S.C. 154(b) by 810 days.

(21) Appl. No.: 14/583,173

(22) Filed: Dec. 25, 2014

(65) Prior Publication Data

US 2016/0066703 A1 Mar. 10, 2016

(30) Foreign Application Priority Data

Sep. 9, 2014 (CN) .......................... 2014 1 0456131

(51) Int. Cl.
*A61G 7/015* (2006.01)
*A61G 7/018* (2006.01)
(Continued)

(52) U.S. Cl.
CPC .............. *A47C 31/00* (2013.01); *A47C 27/06* (2013.01); *A61B 5/4806* (2013.01);
(Continued)

(58) Field of Classification Search
CPC ........ A61G 7/015; A61G 7/018; A61G 7/012; A61G 7/005; A61G 2203/10;
(Continued)

(56) References Cited

U.S. PATENT DOCUMENTS 3,089,130 A * 5/1963 Wilson ...................... A61F 5/56
128/204.23
5,853,005 A * 12/1998 Scanlon ................. A61B 5/113
29/235.5

(Continued)

Primary Examiner — Robert G Santos
(74) Attorney, Agent, or Firm — Global IP Services; Tianhua Gu

(57) ABSTRACT

The invention relates to a sleep support system and the control method thereof. People may come across such emergencies as insomnia for some reason when going to sleep or apnea during sleep for some reason. The invention comprises a bedding, a processor, a sleep aid mechanism, a data acquisition mechanism and a wake-up mechanism, wherein the data acquisition mechanism comprises a data converter, a vibration sensor assembly and a snore sensor which are connected to the data converter; the processor receives signals of the vibration sensor assembly through the data converter and controls the sleep aid mechanism; and the processor receives signals of the snore sensor through the data converter and controls the wake-up mechanism. By installing the sleep support system in a bedroom, intervention or emergency treatment measures can be taken timely through real-time monitoring of the data of various physical signs of the user and identification of the sleep state of the user when abnormity is detected, to ensure that the user can have high quality sleep, effectively prevent the occurrence of accidents of the user during sleep, and ensure good sleep quality of the user.

6 Claims, 3 Drawing Sheets

(51) Int. Cl.
*A47C 27/06* (2006.01)
*A61B 5/0205* (2006.01)
*A47C 31/00* (2006.01)
*A61B 5/00* (2006.01)
*G08B 21/04* (2006.01)
*A61M 21/02* (2006.01)
*A61B 5/024* (2006.01)
*A61B 5/08* (2006.01)
*A61B 5/11* (2006.01)
*A61M 21/00* (2006.01)

(52) U.S. Cl.
CPC ............ *A61B 5/6892* (2013.01); *A61G 7/015* (2013.01); *A61M 21/02* (2013.01); *G08B 21/0461* (2013.01); *A61B 5/024* (2013.01); *A61B 5/0816* (2013.01); *A61B 5/11* (2013.01); *A61M 2021/0022* (2013.01); *A61M 2021/0027* (2013.01); *A61M 2021/0066* (2013.01); *A61M 2021/0083* (2013.01); *A61M 2205/3592* (2013.01); *A61M 2205/50* (2013.01); *A61M 2230/06* (2013.01); *A61M 2230/42* (2013.01); *A61M 2230/63* (2013.01)

(58) Field of Classification Search
CPC .. A61G 2203/12; A47C 20/04; A47C 20/041; A47C 27/06; A47C 31/008; A61B 5/746; A61B 5/024; A61B 5/0022; G08B 21/02
USPC .......... 5/613, 616, 617, 600, 716; 340/573.1, 340/575
See application file for complete search history.

(56) References Cited

U.S. PATENT DOCUMENTS

| | | | |
|---|---|---|---|
| 8,418,289 B2 * | 4/2013 | Lin | A61B 5/0002 5/613 |
| 2012/0324649 A1 * | 12/2012 | Lin | A61B 5/0002 5/613 |
| 2013/0043988 A1 * | 2/2013 | Bruno | A47G 9/0253 340/407.1 |
| 2014/0366273 A1 * | 12/2014 | Davis, II | G04G 13/02 5/639 |
| 2016/0066703 A1 * | 3/2016 | Chen | A47C 27/06 5/613 |
| 2018/0064404 A1 * | 3/2018 | Zheng | A61B 5/746 |
| 2018/0078197 A1 * | 3/2018 | Ware | A61B 5/0205 |
| 2018/0078198 A1 * | 3/2018 | Reich | A61B 5/0022 |
| 2018/0081527 A1 * | 3/2018 | Dolecki | G06F 3/04847 |

* cited by examiner

SLEEP SUPPORT SYSTEM AND CONTROL METHOD THEREOF

CROSS REFERENCE TO RELATED PATENT APPLICATION

The present application claims the priority of CN application No. 2014104561310 filed on Sep. 9, 2014, which application is incorporated herein by reference.

FIELD OF THE INVENTION

The invention relates to a sleep support system, in particular to a system safeguarding the quality of sleep and the control method thereof.

BACKGROUND OF THE INVENTION

Sleep is a barometer of human health, and is also an important process for recovery and regulation of human body itself. People will inevitably have insomnia, snoring and other conditions during sleep, wherein, insomnia is a kind of subjective experience of the people suffering from unsatisfied duration and quality of sleep which will thus affect the social function during the day, including difficulty in falling asleep, frequent awakening and early morning wake-up, and can cause human fatigue, slow response, headache, unconcentrated attention, and even schizophrenia when in serious case. When a person is in the state of insomnia for a long time, the state of human body function and mental state will be greatly affected, thus greatly affecting his/her daily live; while snoring is caused by wrong sleeping postures, resulting in narrowing of respiratory passages, and severe snoring can cause repeated suspension of breathing, severe hypoxia of the brain and blood, forming hypoxemia and further inducing hypertension, cerebral and cardiac diseases, cardiac arrhythmias, myocardial infarction and angina pectoris, and if apnea at night time exceeds 120 seconds, sudden death may even occur, thus having a great impact on health. In daily life, on the one hand, people often easily overlook the impact of insomnia and snoring on human health, and are subjected to suboptimal health condition for a long time due to poor sleep quality; on the other hand, people are in unconscious state during sleep, so that people cannot perceive their own health conditions, thus further leading to sudden appearance of apnea in human body and failure in taking timely and effective self-help measures, which will likely result in a chain of symptoms, and some people may even lose their lives therefor. Currently, the bedding closely related to sleeping attaches much importance to lying comfort and support property, and there is not yet solution for effectively preventing insomnia and respiratory inhibition during severe snoring.

SUMMARY OF THE INVENTION

In order to solve the deficiencies of the prior art, the invention provides a sleep support system and the control method thereof, to perform real-time monitoring of the sleep state of human body, and take appropriate measures in the event of abnormalities to address in a timely manner, so as to ensure the quality of sleep.

The invention is achieved as follows: A sleep protection system is characterized in that the system comprises a bedding, a processor, a sleep aid mechanism, a data acquisition mechanism installed in the bedding, and a wake-up mechanism, wherein the data acquisition mechanism comprises a data converter, a vibration sensing component and a snore sensor which are connected to the data converter; the processor receives signals of the vibration sensing component through the data converter and controls the sleep aid mechanism; and the processor receives signals of the snore sensor through the data converter and controls the wake-up mechanism. By installing the sleep support system in a bedroom, when a user lying on the bedding is in the sleep state, various physical signs of the user can be collected by using the data acquisition mechanism, real-time data monitoring can be achieved through the processor, whether or not the user is in the state of insomnia or apnea and other abnormalities can be discriminated according to the detected data, and then intervention or treatment can be made by driving the corresponding sleep aid mechanism or wake-up mechanism. On one hand, the user can quickly go to sleep via the sleep aid mechanism, to effectively improve sleep quality; on the other hand, the system can facilitate to wake up the user from the sleep state through the wake-up mechanism when abnormalities occur, so as to ensure safe sleep of users.

Preferably, the processor is a handheld mobile device, the processor, the data converter, the sleep aid mechanism and the wake-up mechanism are connected in communication via wifi modules. The handheld mobile device can be a mobile phone or tablet computer, or can be an independent functional device matched with the system, components of all mechanisms are connected with the processor device in communication via wifi modules, and the characteristics of quick wifi data transfer and large signal coverage are utilized, to ensure that the processor can timely control the components of all mechanisms dispersed in the bedroom.

Preferably, the bedding comprises a bed tray and a mattress stacked at the upper part of the bed tray, wherein the mattress comprises a plurality of cylindrical springs and a fabric cover, the data converter is arranged in a tank body with a cavity arranged inside; the tank body is matched with the contour of the cylindrical springs which fit together to form a spring matrix body spread on the mattress, the tank body is positioned at a right-angle end of the spring matrix body, and the spring matrix body is wholly wrapped by the fabric cover. The original mattress adopts a spring matrix body formed by regularly arranging a plurality of cylindrical springs, while in this technical scheme, the cylindrical spring at a right angle of the spring matrix body on one end is replaced with the tank body installed with the data converter, not only the comfort of the original spring matrix body is not affected, but also the tank body is concealed in mattress, the structural space in the bedding is effectively used; and in order to prevent a user from touching the built-in tank body due to pressing of the mattress, the tank is installed at the right angle end of the spring matrix body which is less touched by a person lying on the bed, therefore the situation of discomfort due to touching of the tank body can be effectively prevented.

Preferably, the vibration sensor assembly is transversely arranged on the upper surface of the spring matrix body in a strip-shaped manner and is wrapped and positioned by the fabric cover, and the length of the vibration sensor assembly is matched with the width of the mattress; the data converter receives signals from the vibration sensor assembly via a wire and then transmits to the processor through the wifi modules; and the vibration sensor assembly comprises a heartbeat frequency sensor, a respiratory frequency sensor and a turnover times sensor, and the sensing area of the heartbeat frequency sensor and the respiratory frequency sensor are the range of 5-20 cm thereabove. The strip-shaped vibration sensor assembly across the entire mattress can respond to the user who turns over on the mattress and is close to the edge of the mattress, the scope of data collection of the vibration sensor assembly can be effectively expanded; since the position of the vibration sensor assembly is fit to the position of the heart of the user lying in bed, the accuracy of data collection of the vibration sensor assembly can be effectively improved; the fabric cover serves to wrap the spring matrix body, can effectively prevent the user from direct contact with the spring matrix body and effectively improve the comfort level of the user; in addition, the vibration sensor assembly is clamped and fixed by the fabric cover together with a matrix cover, which is conducive to concealing and protecting the vibration sensor assembly, and also can ensure that the vibration sensor assembly does not deviate from the service position when being touched by the user; heartbeat frequency sensor, the respiratory frequency sensor and the turnover times sensor are integrally arranged on the strip-shaped vibration sensor assembly, since the cardiopulmonary positions of human body are located within the range of 5-20 cm above the vibration sensor assembly when the user is lying or laterally lying on the mattress, the parameter is preferably selected, to facilitate the heartbeat frequency sensor and the respiratory frequency sensor to collect data. The heartbeat frequency sensor is used for collecting heartbeat signals of the user, the respiratory frequency sensor is used for collecting breathing frequency signals of the user, and the turnover times sensor is used for collecting turnover times signals of the user.

Preferably, the snore sensor is mounted on the upper surface of the first section of the spring matrix body and is wrapped and positioned by the fabric cover, the data converter receives signals from the snore sensor via a wire and then transmits to the processor through the wifi module. When the user is lying on the mattress, his/her head is positioned above the first section of the spring matrix body, and the occurrence site of snoring is near the respiratory passage of the head, therefore the snore sensor is preferably arranged in the nearest position away from the occurrence site, being conducive to collection of snoring signals; the snore sensor adopts the principle of sound induction and is clamped and fixed by the fabric cover and the spring matrix body, so as to conceal and protect the snore sensor; and due to many gaps in the fabric cover, the effect of reducing snoring transmission can be neglected.

Preferably, the sleep aid mechanism comprises one or a plurality of: sleep gas diffuser, sounder, temperature regulator, humidity regulator, carbon dioxide monitor and air purifier. Through the above devices, the sleep aid mechanism can provide adequate sleep promoting gas, hypnotic music, temperature, humidity, carbon dioxide concentration in the bedroom, enabling the user to quickly fall into sleep.

Preferably, the wake-up mechanism comprises a controller mounted in the tank body, a split-type bed plate mounted on the bed tray, a driving assembly used for driving the split-type bed plate to swing, and a stimulation part mounted on the split-type bed plate, wherein the driving assembly and the stimulation part are controlled by the controller; the split-type bed plate comprises a plurality blocks of movable plates, the first movable plate close to the first section of the mattress can swing within the preset angle, and the preset angle is between 15°-45°. The processor is communicated with the controller through the wife modules, so as to control the driving assembly and stimulation part; the split-type bed plate capable of conducting partial movement can play the role of adjusting the sleeping postures of the user in case of apnea, the first movable plate can be used to lift the head and chest of the user, allowing the narrowed respiratory passage due to pressing to restore, and by changing the sleeping postures of the user, the user can be ensured to maintain smooth breathing during sleep; and the stimulation part is used for waking up the user in the sleep state, so that emergency measures can be taken in time against unexpected situations arising during sleep threatening the life of the user.

The control method in the invention is achieved in the following way: the vibration sensor assembly comprises a respiratory frequency sensor used for collecting respiratory frequency signals which are transmitted to the data converter, the data converter performs filtering and analog-to-digital conversion of the signals and then sends to the processor through the wifi modules, and the processor performs comparison and processing of the signals:

(1) The Processor Performs Processing in Terms of Sleep Aid

The processor activates the sleep aid mechanism through the wifi modules after receiving respiratory frequency signals; since the breathing frequencies are disordered and has difference before human falling into sleep and then become smooth and regular along with the in-depth of sleep; after the processor receives respiratory frequency signals at least 15 consecutive times with the same interval, the processor delays in closing the sleep aid mechanism via the wifi modules; and the delay time of closing can be preset on the processor by the user, and can also be set in the all-night turn-on mode to help the user get a better sleep experience.

(2) The Processor Performs Processing in Terms of Wake-up

A preset breath interval value is previously set and is between 15-60 seconds, and the processor calculates the actual breath interval value according to the respiratory frequency signals received:

a. When the actual value is lower than the preset breath interval value, human body is in normal breathing state, and the wake-up mechanism in a dormant state;

b. When the actual breath interval value is greater than or equal to the preset breath interval value and is lower than 60 seconds, it indicates that apnea occurs in human body, at this time, the processor is required to automatically intervene human body, activates the wake-up mechanism through the wifi modules, and drives the split-type bed plate to rise, the lifted split-type bed plate can force the sleeping postures of human body to change, so as to relieve the phenomenon of apnea. Within the next 1-3 minutes, the processor continuously monitors the signal data, if the actual breath interval value drops and is lower than the preset breath interval value, the surface phenomenon of apnea disappears, the processor is not required to continue to intervene and will drive the split-type bed plate to descend via the controller, so that the user can continue to sleep; if the actual breath interval value is still greater than or equal to the preset breath interval value, it indicates the surface phenomenon of apnea does not disappear, wake-up action is performed through the stimulation part to prevent the user from accidents and is continuously performed through the stimulation part in the wake-up process, until the user must stop the action of the stimulation part by manually operating the processor;

c. When the actual breath interval value is greater than 60 seconds, it indicates that the user has the asphyxiation hazard at any time, and the processor drives the simulation part to perform continuous wake-up action via the controller and sends out an alarm signal. In this case, lifting of the split-type bed plate is simultaneously performed along with action of the stimulation part; the processor sends an alarm signal to the outside, including notification to family members or social emergency agencies through phone text messages; and the wake-up action by the stimulation part can be stopped by manually operating the processor.

The vibration sensor assembly comprises a heartbeat frequency sensor used for collecting heartbeat frequency signals, the heartbeat frequency signals are sent to the processor via the data converter, the processor performs comparison and processing of the received actual heartbeat frequency values, and a pre-set heartbeat frequency range is required to be predetermined:

a. When the actual heartbeat frequency value is lower than the lower limit value of the preset heartbeat frequency range, human body is prone to undergo sudden death, the processor drives the stimulation part to continuously perform wake-up action and sends an alarm signal to the outside; and the wake-up action by the stimulation part can be stopped by manually operating the processor;

b. When the user has nightmares in the sleep state, the quality of sleep is seriously affected, the heartbeat frequency will increase with fluctuations in thinking, when the actual heartbeat frequency value is greater than the upper limit of the preset heartbeat frequency range, the processor drives the stimulation part to perform continuous wake-up action, so that the user can escape from annoying nightmares timely until he/she wakes up, the wake-up action by the stimulation part can be stopped by manually operating the processor, and then the user can fall asleep again with improved sleep quality.

The vibration sensor assembly comprises a turnover times sensor used for collecting turnover times signals, the snore sensor is used for collecting snoring frequency signals, the respiratory frequency signals, heartbeat frequency signals, turnover times signals and snoring frequency signals are sent outwardly to a cloud server by the processor for archiving and collation, a sleep health report can be provided for the user through analysis of the data collected over a period of time, and under the guidance of professional doctors, early prevention and treatment can be made against unexpected situations which may occur during sleep, so as to provide the user with a better sleep experience.

The invention has the obvious beneficial effects: by installing the sleep protection system in a bedroom, intervention or emergency treatment measures can be taken timely through real-time monitoring of the data of various physical signs of the user and identification of the sleep state of the user when abnormity is detected, to ensure that the user can have high quality sleep, effectively prevent the occurrence of accidents of the user during sleep, and ensure good sleep quality of the user.

In the figures: 1. mattress, 2. bed tray, 3. fabric cover, 4. data converter, 5. tank body, 6. cylindrical spring, 7. spring matrix body 8. controller, 9. first movable plate, 10. stimulation part, 11. driving assembly, 12. vibration sensor assembly, 13. snore sensor, 14. wire.

DETAIL DESCRIPTION OF THE INVENTION

The essential characteristics of the invention are further illustrated in combination with the attached figures and the specific embodiments.

Figure 1:
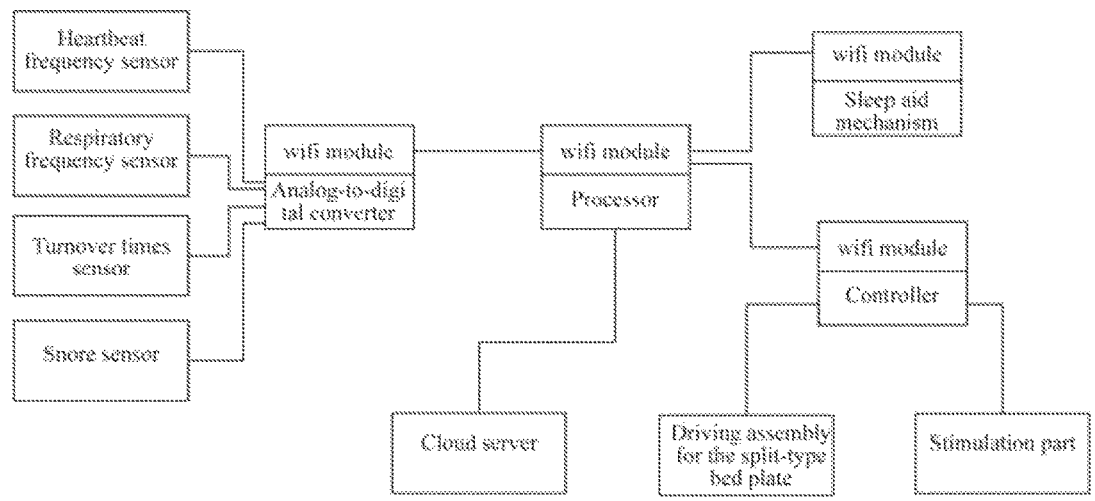
FIG. 1 is a schematic diagram of the modular structure of the invention.
Figure 3:
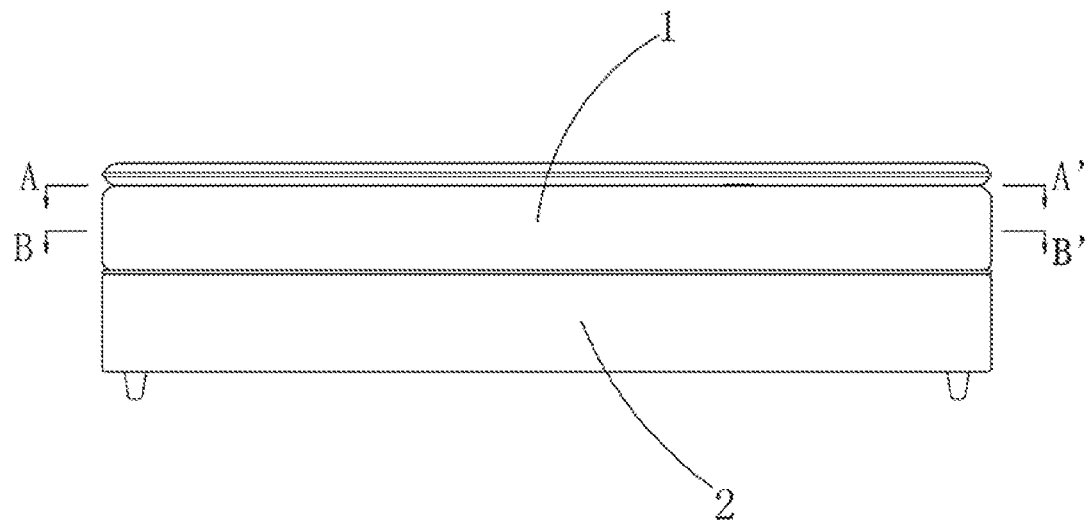
FIG. 3 is a front view of the bed tray and the mattress.
Figure 4:
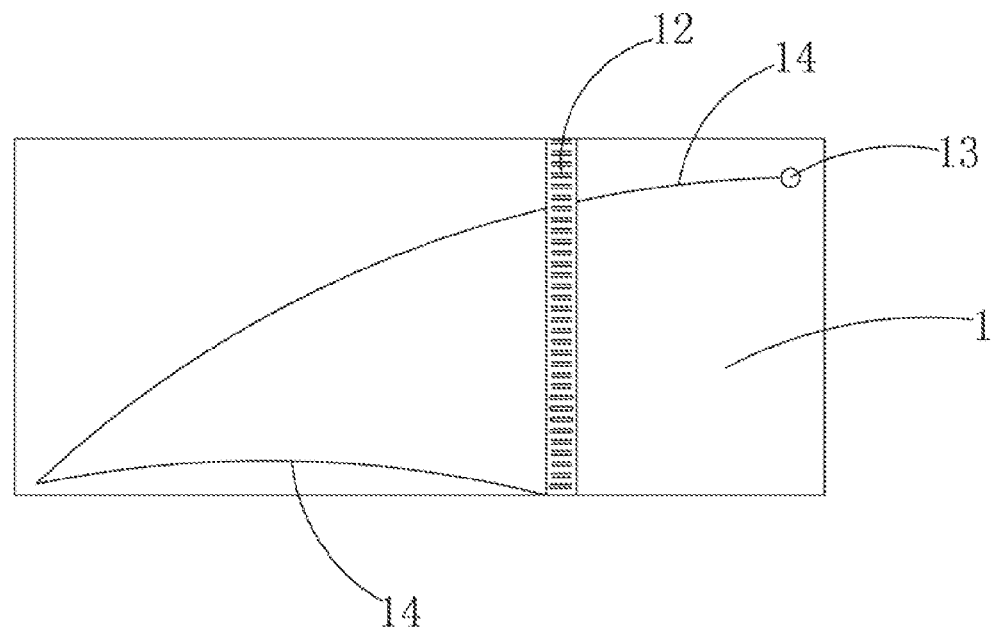
FIG. 4 is a schematic diagram of A-A' cross-sectional structure.

As shown in FIG. 1, a sleep support system is composed of a bedding, a processor, a sleep aid mechanism, a data acquisition mechanism built in the bedding and a wake-up mechanism, wherein the data acquisition mechanism comprises a data converter 4, and a vibration sensor assembly 12 and a snore sensor 13 which are connected to the converter 4; the processor receives signals from the vibration sensor assembly 12 through the data converter 4 and controls the sleep aid mechanism, the processor receives signals from the snore sensor 13 through the data converter 4 and controls the wake-up mechanism; the processor is a handheld mobile device, the processor, the data converter 4, the sleep aid mechanism and the wake-up mechanism are connected in communication through wifi modules; the bedding comprises a bed tray 2 and a mattress 1 stacked at the upper part of the bed tray 2 (as shown in FIG. 3), the mattress 1 comprises a plurality of cylindrical springs 6 and a fabric cover 3, the data converter 4 is arranged in a tank body 5 with a cavity arranged inside, the tank body 5 is matched with the contours of the cylindrical springs 6 which fit together to form a spring matrix body 7 spread on the mattress 1, the tank body 5 is positioned at a right-angle end of the spring matrix body 7, and spring matrix body 7 is entirely wrapped by the fabric cover 3; the vibration sensor assembly 12 is transversely arranged on the upper surface of the spring matrix body 7 in a strip-shaped manner and is wrapped and positioned by the fabric cover 3 (as shown in FIG. 4), and the length of the vibration sensor assembly 12 is matched with the width of the mattress 1; the data converter 4 receives signals from the vibration sensor assembly 12 via a wire 14 and then transmits to the processor through the wifi modules; and the vibration sensor assembly 12 comprises a heartbeat frequency sensor, a respiratory frequency sensor and a turnover times sensor, and the sensing area of the heartbeat frequency sensor and the respiratory frequency sensor are the range of 5-20 cm thereabove; the snore sensor 13 is mounted on the upper surface of the first section of the spring matrix body 7 and is wrapped and positioned by the fabric cover 3, the data converter 4 receives signals from the snore sensor 13 via a wire 14 and then transmits to the processor through the wifi modules.

In practical operation, the processor is preferably a mobile phone or tablet computer and other mobile devices of the user, because these mobile devices themselves have wifi modules, thus facilitating operation. Before use, the user requires to pre-install an application in these mobile devices matched with the system, the application can achieve the functions of receiving data of human vital signs, data comparison, presetting of sleep aid parameters, presetting of wake-up conditions, etc., so that every user can customize the system according to their own circumstances, and the applicable groups for the system are increased.

In practical operation, the sleep aid mechanism comprises one or a plurality of: sleep gas diffuser, sounder, temperature regulator, humidity regulator, carbon dioxide monitor and air purifier, the device to be used can be determined according to the user's own situations or the environment the user stays, for example: a. when the humidity of the environment under which the user stays is higher, a humidifier is required to be used, to make the humidity in the bedroom suitable for human sleep; b. when the user prefers to go to sleep while listening to the rhythmic dripping sound, a sounder can be installed in the bedroom, so as to induce the user to fall into sleep as soon as possible. The above devices can be professional equipment matched with the system and controlled by the processor in a unified way, and also can be the existing equipment in the bedroom of the user, and unified control can be achieved through control and transformation of these devices. Control of the sleep aid mechanism by the processor includes switch control and degree control, for example, the processor can control turn-on, turn-off of the humidity regulator as well as maintaining of indoor humidity in a constant value to help the user fall into sleep, and the constant value can be a preset value of the system or a preset value set by the user according to his/her own situations. The invention adopts the preferable scheme that all electrical devices of the sleep aid mechanism are installed in a sleep aid box, and constitute to form a complete set of products along with the mattress 1 and the bed tray 2, so as to be easy to carry and use, meanwhile the compatibility between the sleep aid mechanism and the processor can be ensured, and stable operation of sleep aid mechanism can be ensured.

In practical operation, the sensing area of the heartbeat frequency sensor and the respiratory frequency sensor are the range of 5-20 cm thereabove; setting of the range is determined based on the heart, chest, lungs and other organs of the user while sleeping, so as to facilitate the heartbeat frequency sensor and the respiratory frequency sensor to collect data of the physical signs of human body, therefore the sensing area can be adjusted according to the user's own conditions and should be considered as the specific embodiments of the invention.

Figure 2:
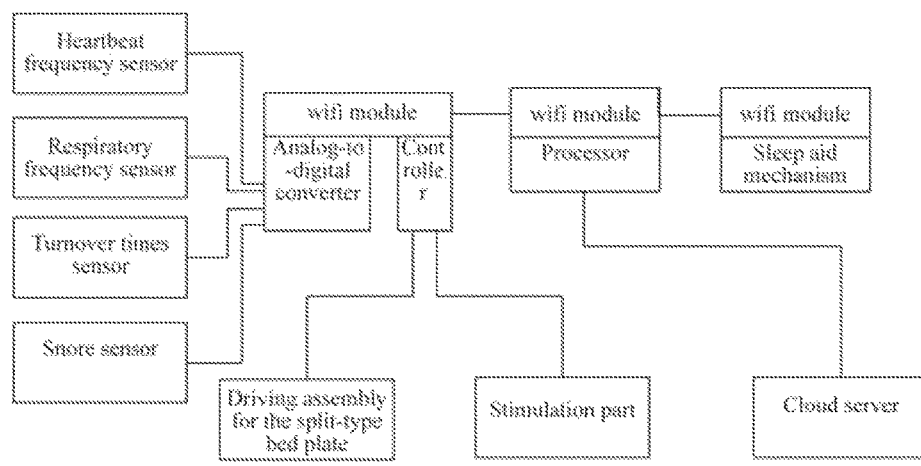
FIG. 2 is a schematic diagram of the modular structure when the controller and the data converter share the wifi modules.
Figure 5:
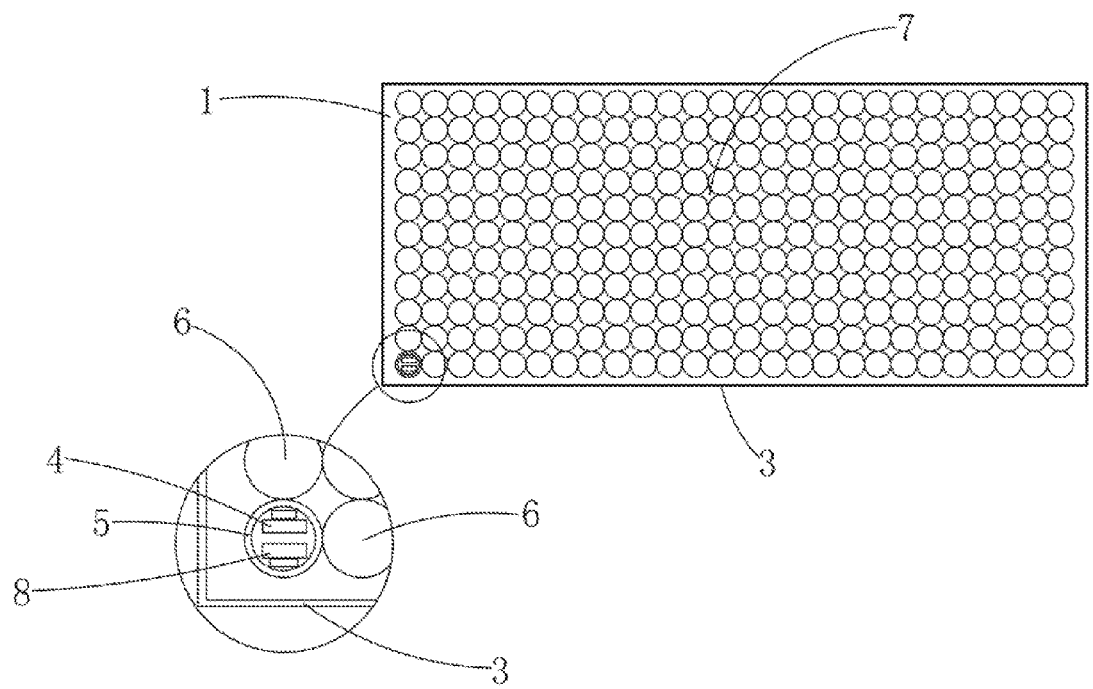
FIG. 5 is a schematic diagram of B-B' cross-sectional structure.

In practical operation, the controller of the data converter 4 and the wake-up mechanism 8 are both arranged in the tank body 5 and share a common wife module (as shown in FIG. 2), thus simplifying the structure, the tank body 5 is made of rigid material and can play a role of protecting the above electrical device, the tank body 5 is positioned at a right-angle end of the spring matrix body 7 (as shown in FIG. 5), and is preferably positioned at the end away from the head of the user, and the damage of electromagnetic radiation to human brain can be reduced by increasing the distance between the electrical device and the head of human body. During installation, there are two methods can be adopted: first method, the tank body 5 is matched with the contours of the cylindrical springs 6 which fit together to form a spring matrix body 7 spread on the mattress 1; second method, the tank body 5 is mounted in a hollow cavity of the cylindrical spring 6 in an inserting manner, and the height of the tank body 5 is lower than that of the cylindrical spring 6 in the compressed state, so as to effectively prevent discomfort of human body in lying by the tank body 5. The two above installation methods shall be regarded as the specific embodiments of the invention.

Figure 6:
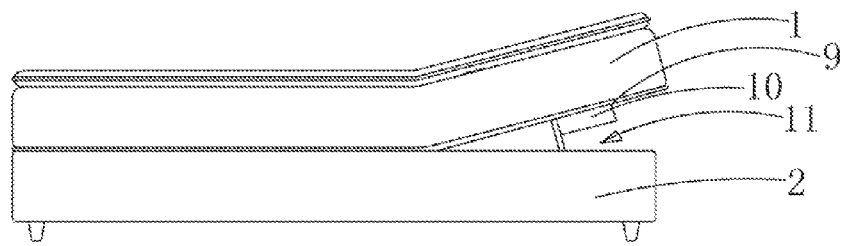
FIG. 6 is a schematic diagram of the structure when the first movable plate is lifted.

In practical operation, the wake-up mechanism comprises a controller 8 mounted in the tank body 5, a split-type bed plate mounted on the bed tray 2, a driving assembly 11 used for driving the split-type bed plate to swing, and a stimulation part 10 mounted on the split-type bed plate, wherein the driving assembly 11 and the stimulation part 10 are both controlled by the controller 8; the split-type bed plate comprises a plurality of blocks of movable plates, and the first movable plate 9 corresponding to the head of the user can swing within a preset angle (as shown in FIG. 6). The driving assembly 11 can be various forms of structures; embodiment I: the driving assembly 11 comprises a stepper motor, and a rack connected to one end of the first movable plate 9, wherein one side edge of the first movable plate 9 is rotationally connected to the second movable plate through shafts, the stepper motor is matched with the rack through a gear, to realize that the first movable plate 9 can perform swinging and vertical actions by taking one side shaft as the centre; embodiment II: the driving assembly 11 comprises an air pump and an air cylinder, wherein one side edge of the first movable plate 9 is rotationally and pivotally connected to the second movable plate, the air cylinder is fixed to the bed tray 2, one end of the piston rod is connected with the first movable plate 9, and the first movable plate 9 can perform swinging and vertical actions through the telescopic cylinder by taking one side shaft as the center; embodiment III: the driving assembly 11 comprises a motor fixedly connected to the bed tray 2, and a sectorial gear plate fixedly connected at the lower part of the first movable plate 9, wherein the motor drives the sectorial gear plate to rotate through the gear and drives the first movable plate 9 to perform swinging and lifting; and as long as the bed plate can rise and fall under the control of the controller 8, the embodiments should be considered as the specific embodiments of the invention.

In practical operation, the first movable plate 9 can swing and rise within 15°-45°, so that the sleeping postures of the user can be changed through lifting of the first movable plate in the event of apnea, the specific lifting angle can be preset by the user in the processor, thus making the change of sleeping postures better.

In practical operation, the stimulation part 10 is used for waking up the user in a sleep state, can be in various forms and can be determined according to the degree of difficulty in waking up user, for example, the stimulation part 10 can be one or combination of a plurality of: vibrator, sound and light emitter, heater, physical beater, etc., so as to achieve the wake-up function. The mounting position of the stimulation part 10 can be adjusted according to individual circumstances, as long as the stimulation part 10 has the effect of wake-up and is harmless to human body, the embodiments should be considered as the specific embodiments of the invention.

In practical operation, the tank body 5 is provided with rechargeable batteries, the batteries provide stable and long-lasting power to the data converter 4 and the controller 8 and are charged through an externally connected supply line, and the data converter 4 provides power to the vibration sensor assembly 12 and the snore sensor 13 through the wire 14. In order to avoid the risk that the system cannot work properly due to depleted batteries of the processor (mobile devices), the preferable scheme adopts that a charging stand matched with the processor is prearranged at one side of the mattress 1, so as to charge the processor and guarantee the normal operation of the processor all night.

A control method for the sleep support system comprises: the vibration sensor assembly 12 comprises a respiratory frequency sensor used for collecting respiratory frequency signals, a heartbeat frequency sensor used for collecting heartbeat frequency signals, a turnover times sensor used for collecting turnover times signals, and a snore sensor 13 used for collecting snoring frequency signals, wherein the above signals are transmitted to the data converter 4, the data converter 4 performs filtering, amplification and analog-to-digital conversion processing of the signals and transmits to the processor through the wifi modules, and the processor performs comparing and processing of the above signals:

(1) The Processor Performs Processing in Terms of Respiratory Frequency Signals

The processor activates the sleep aid mechanism through the wifi modules after receiving respiratory frequency signals; since the breathing frequencies are disordered and has difference before human fall into sleep and then become smooth and regular along with the in-depth of sleep; after the processor receives respiratory frequency signals at least 15 consecutive times with the same interval, the processor delays in closing the sleep aid mechanism via the wifi modules; and the delay time of closing can be preset on the processor by the user, and can also be set in the all-night turn-on mode to help the user get a better sleep experience.

A preset breath interval value is previously set and is between 15-60 seconds, and the processor calculates the actual breath interval value according to the respiratory frequency signals received:

a. When the actual value is lower than the preset breath interval value, human body is in normal breathing state, and the wake-up mechanism in a dormant state;

b. When the actual breath interval value is greater than or equal to the preset breath interval value and is lower than 60 seconds, it indicates that apnea occurs in human body, at this time, the processor is required to automatically intervene human body, activates the wake-up mechanism through the wifi modules, and drives the split-type bed plate to rise, the lifted split-type bed plate can force the sleeping postures of human body to change, so as to relieve the phenomenon of apnea. Within the next 1-3 minutes, the processor continuously monitors the signal data, if the actual breath interval value drops and is lower than the preset breath interval value, the surface phenomenon of apnea disappears, the processor is not required to continue to intervene and will drive the split-type bed plate to descend via the controller 8, so that the user can continue to sleep; if the actual breath interval value is still greater than or equal to the preset breath interval value, it indicates the surface phenomenon of apnea does not disappear, wake-up action is performed through the stimulation part 10 to prevent the user from accidents and is continuously performed through the stimulation part 10 in the wake-up process, until the user must stop the action of the stimulation part by manually operating the processor;

c. When the actual breath interval value is greater than 60 seconds, it indicates that the user has the asphyxiation hazard at any time, and the processor drives the simulation part to perform continuous wake-up action via the controller 8 and sends an alarm signal to the outside. In this case, lifting of the split-type bed plate is simultaneously performed along with action of the stimulation part; the processor sends an alarm signal to the outside, including notification to family members or social emergency agencies through phone text messages; and the wake-up action by the stimulation part can be stopped by manually operate the processor.

(2) The Processor Performs Processing in Terms of Heartbeat Frequency Signals

The processor performs comparison and processing of the above signals, treatment, the conditions of vital signs are different due to different users, and the user can previously set a preset heartbeat frequency range according to his/her own situations:

a. When the actual heartbeat frequency value is lower than the lower limit of the preset heartbeat frequency range, it indicates that the heartbeat frequency of human body is too slow, human body is prone to have the risk of sudden death, and in order to ensure sleep safety of the user, the processor drives the stimulation part 10 to continuously perform wake-up action through the controller 8 and sends an alarm signal to the outside;

b. When the user has nightmares in the sleep state, the quality of sleep is seriously affected, the heartbeat frequency will increase with fluctuations in thinking, when the actual heartbeat frequency value is greater than the upper limit of the preset heartbeat frequency range, the processor drives the stimulation part 10 to perform continuous wake-up action, so that the user can escape from annoying nightmares timely until he/she wakes up, the wake-up action by the stimulation part 10 can be stopped by manually operating the processor, and then the user can fall asleep again with improved sleep quality.

In practical operation, since the wake-up action by the stimulation part 10 is required to be stopped by manually operating the processor, after the stimulation part 10 is turned on, continuous wake-up action on the user is performed, the wake-up action by the stimulation part 10 is stopped by manually operating the processor only when the user is wakened up or other people come to rescue, and the wake-up efficiency of the wake-up mechanism can be ensured. The preferable scheme adopts that the amplitude, frequency and degree of wake-up action of the stimulation part 10 can be increased along with the extension of the wake-up action time, so as to further improve the wake-up efficiency.

In practical operation, in case of a need of sending an alarm signal to the outside, the outside objects of sending can be multiple, preferably the persons capable of taking timely relief measures for the user, such as family members, emergency agencies, etc., preferably by telephone and short messages, and alarm signals are continuously sent to the outside until the stimulation part 10 is turned off manually.

In practical operation, the respiratory frequency signals, heartbeat frequency signals, turnover times signals and snoring frequency signals are outwardly sent to a cloud server through the processor for archiving, collation and analysis, and diagnosis of the sleep state is fed back based on the data accumulated. The processor adopts Internet as the preferable way of sending alarm signals, sleep diary with an independent data archive is created by the cloud server for each user, a sleep health report can be obtained through analysis of the data of each user, the case of suspected sleep disorders can be submitted to the professional medical organization for diagnosis, and then specific treatment recommendations and proposals can be provided. The sleep health report, treatment recommendations and proposals can be sent back to the processor via Internet, to enable the user to understand his/her state of sleep.

What is claimed is:

1. A sleep support system comprising:
a bedding, a processor, a sleep aid mechanism, a data acquisition mechanism installed in the bedding, and a wake-up mechanism;
the data acquisition mechanism comprises a data converter (4), a vibration sensor assembly (12) and a snore sensor (13) which are connected to the data converter (4);
the processor receives signals of the vibration sensor assembly (12) through the data converter (4) and controls the sleep aid mechanism and the processor receives signals of the snore sensor (13) through the data converter (4) and controls the wake-up mechanism wherein, the bedding comprises a bed tray (2) and a mattress (1) stacked on the bed tray (2), the mattress (1) comprises a plurality of cylindrical springs (6) and a fabric cover (3);

the data converter (4) is arranged in a tank body (5) with a cavity arranged inside;

the tank body (5) is matched with the contours of the cylindrical springs (6) which fit together to form a spring matrix body (7) spread on the mattress (1), the tank body (5) is positioned at a right-angle end of the spring matrix body (7); and the spring matrix body (7) is wholly wrapped by the fabric cover (3).

2. A sleep support system of claim 1 is characterized in that the processor is a handheld mobile device, and the processor, the data converter (4), the sleep aid mechanism and the wake-up mechanism are connected through communication via wifi modules.

3. A sleep support system of claim 2 is characterized in that the vibration sensor assembly (12) is transversely arranged on the upper surface of the spring matrix body (7) in a strip-shaped manner and is wrapped and positioned by the fabric cover (3), and the length of the vibration sensor assembly (12) is matched with the width of the mattress (1); the data converter (4) receives signals from the vibration sensor assembly (12) via a wire (14) and then transmits to the processor through the wifi modules; and the vibration sensor assembly (12) comprises a heartbeat frequency sensor, a respiratory frequency sensor and a turnover times sensor, and the sensing area of the heartbeat frequency sensor and the respiratory frequency sensor are the range of 5-20 cm above.

4. A sleep support system of claim 3 is characterized in that the snore sensor (13) is installed on an upper surface of a first section of the spring matrix body (7) and is wrapped and positioned by the fabric cover (3); the data converter (4) receives signals from the snore sensor (13) through the wire (14), and then sends the received signals to the processor through the wifi modules.

5. A sleep support system of claim 4 is characterized in that the sleep aid mechanism comprises one or a plurality of sleep gas diffuser, sounder, temperature regulator, humidity regulator, carbon dioxide monitor and air purifier.

6. A sleep support system of claim 4 is characterized in that the wake-up mechanism comprises a controller (8) mounted in the tank body (5), a split-type bed plate mounted on the bed tray (2), a driving assembly (11) used for driving the split-type bed plate to swing, and a stimulation part (10) mounted on the split-type bed plate, wherein the driving assembly (11) and the stimulation part (10) are controlled by the controller (8); the split-type bed plate comprises a plurality of blocks of movable plates, a first movable plate (9) closest to a first section of the mattress (1) can swing within a preset angle, and the preset angle is between 15°-45°.

* * * * *